US00PP16299P2

(12) United States Plant Patent
Gilford et al.

(10) Patent No.: US PP16,299 P2
(45) Date of Patent: Feb. 28, 2006

(54) STRAWBERRY PLANT NAMED 'DRISCOLL DESTIN'

(50) Latin Name: *Fragaria×ananassa*
Varietal Denomination: Driscoll Destin

(76) Inventors: Kristie L. Gilford, 1525 N. Dover Rd., Dover, FL (US) 33527; Bruce D. Mowrey, 266 Webb Rd., Watsonville, CA (US) 95076; JoAnne Coss, 217 Katherine Ave., Salinas, CA (US) 93901

( * ) Notice: Subject to any disclaimer, the term of this patent is extended or adjusted under 35 U.S.C. 154(b) by 100 days.

(21) Appl. No.: 10/923,531

(22) Filed: Aug. 19, 2004

(51) Int. Cl.
*A01H 5/00* (2006.01)

(52) U.S. Cl. ..... Plt./209

(58) Field of Classification Search ..... Plt./209
See application file for complete search history.

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll Destin.' The variety is similar to the varieties 'Biscayne' and 'Key Largo.' The variety is distinguished from 'Biscayne' and 'Key Largo,' in particular, by its shorter plant height, larger flower diameter, an orange-red external fruit color, greater yield, weak leaf glossiness, very dense stipule pubescence, and a small hollow fruit center.

5 Drawing Sheets

1. Latin name of the genus and species of the plant claimed: The variety is botanically identified as *Fragaria× ananassa.*

1.1 Variety denomination: The strawberry variety denomination is 'Driscoll Destin'.

2. BACKGROUND OF THE INVENTION

The new variety originated as a result of a controlled cross between the strawberry plants '73D144' (unpatented variety) and '88E94' (unpatented variety) in an ongoing breeding program, and was discovered as a seedling in Monterey, Calif. in 2000. The original seedling of the new cultivar was asexually propagated by stolons in a Nursery in Shasta County, Calif. Propagules were transplanted to a controlled breeding plot in Monterey county, Calif., where the variety was identified and selected for further evaluation. 'Driscoll Destin' was subsequently asexually propagated and underwent further testing in Hillsborough county, Fla. for three years. This propagation and testing has demonstrated that the combination of traits disclosed herein which characterize the new variety are fixed and retained true to type through successive generations of asexual reproduction.

3. SUMMARY OF THE INVENTION

The present invention relates to a new and distinct variety of strawberry named 'Driscoll Destin.' The variety is botanically identified as *Fragaria×ananassa.* The new variety is distinguished from other varieties by a number of characteristics as set forth in Tables 1–4.

4. COMPARISON TO SIMILAR VARIETIES

The varieties which we believe to be similar to 'Driscoll Destin' from those known to us are 'Biscayne' (U.S. Plant Pat. No. 12,186) and 'Key Largo' (U.S. Plant Pat. No. 8,649). There are several characteristics of the new variety that are different from, or not possessed by 'Biscayne' and 'Key Largo'. The new variety has a shorter plant height, larger flower diameter, an orange-red external fruit color, greater yield, weak leaf glossiness, very dense stipule pubescence, and a small hollow fruit center.

'Driscoll Destin' is distinguished from its maternal parent '73D144' by its larger average berry size and improved shipability. 'Driscoll Destin' is distinguished from its paternal parent '88E94' by its larger average berry size, improved shipping ability, and partial everbearing in comparison to the full everbearing of '88E94'.

5. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

6. DESCRIPTION OF THE NEW VARIETY

Figure 1:
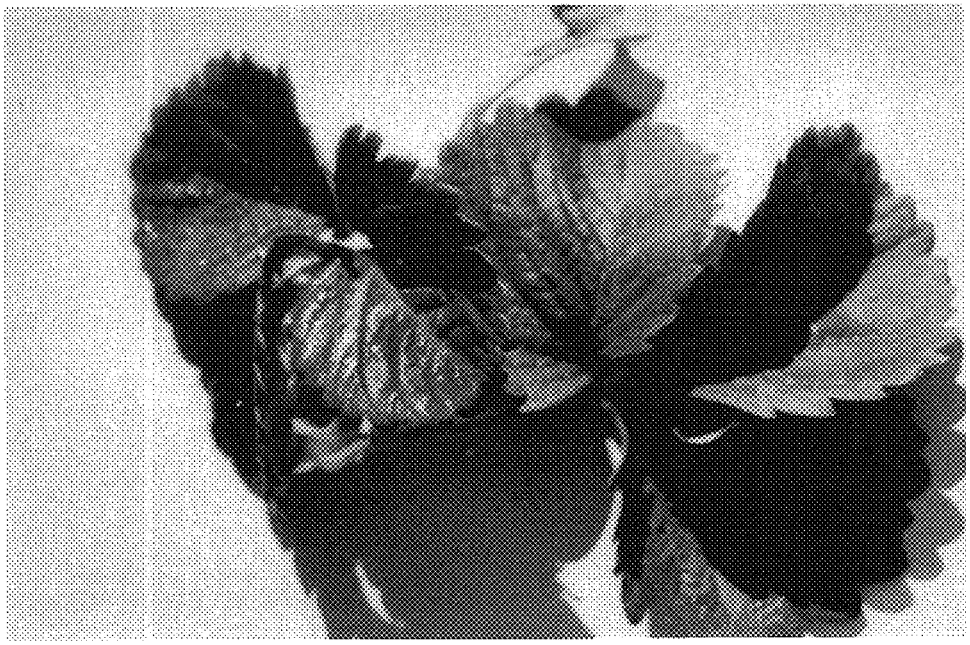
FIG. 1 shows the upper side of the leaves of the plant.
Figure 2:
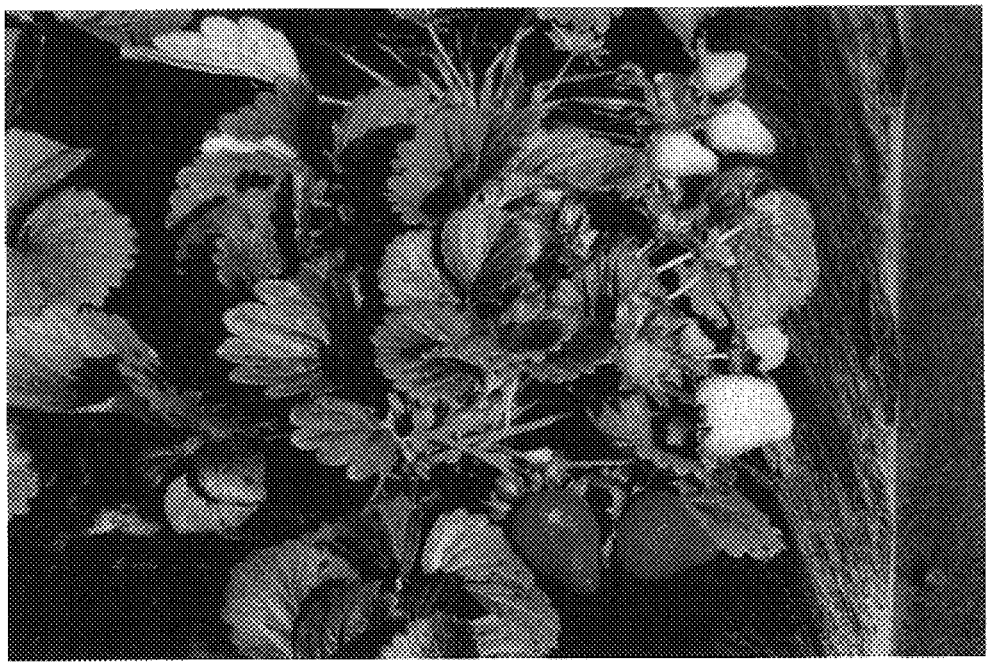
FIG. 2 shows the whole the plant.
Figure 3:
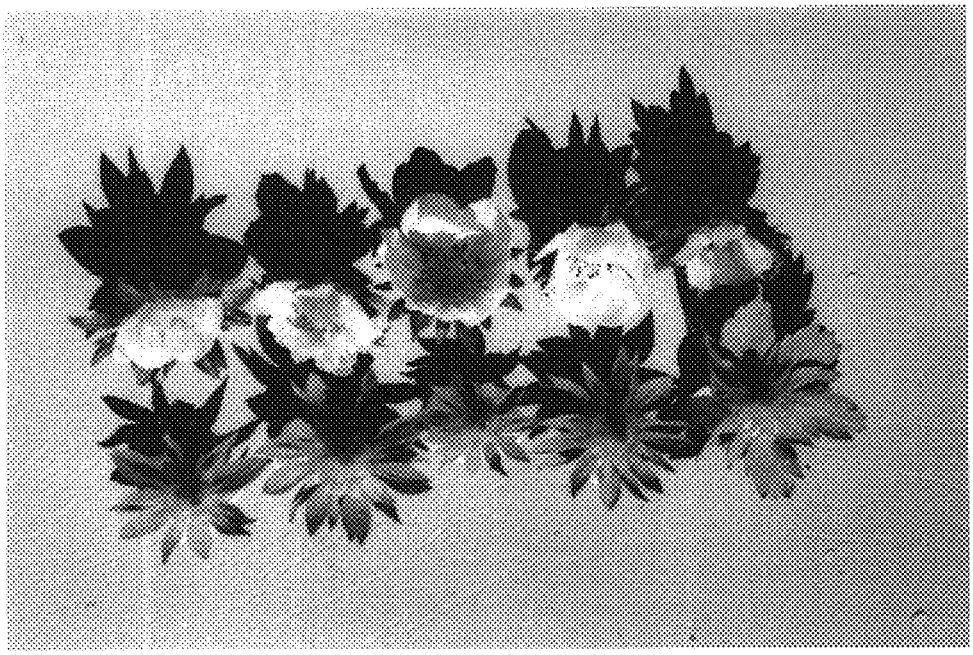
FIG. 3 shows the under side and underside of the flowers.
Figure 4:
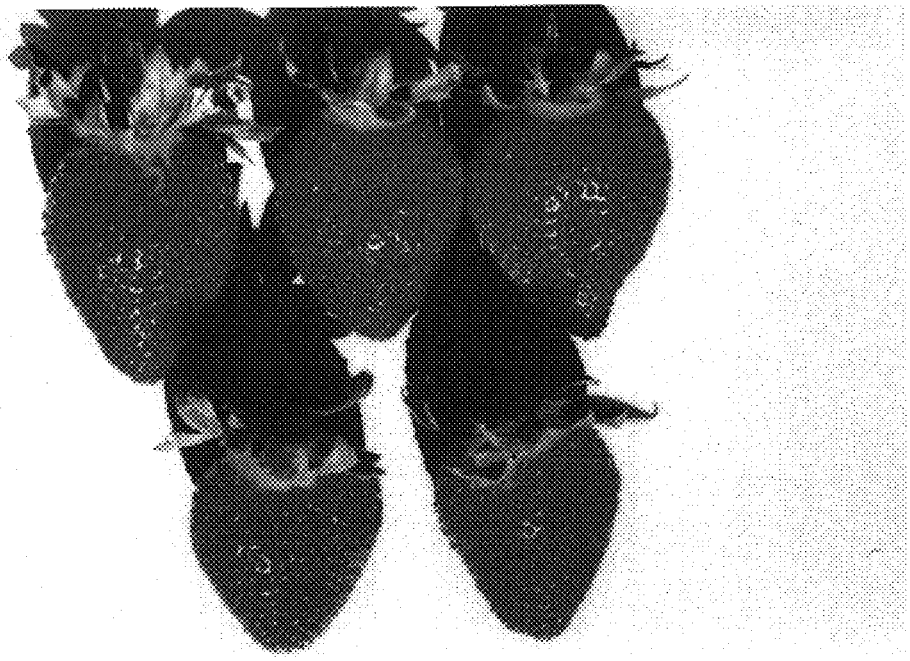
FIG. 4 shows a close-up of the fruit.
Figure 5:
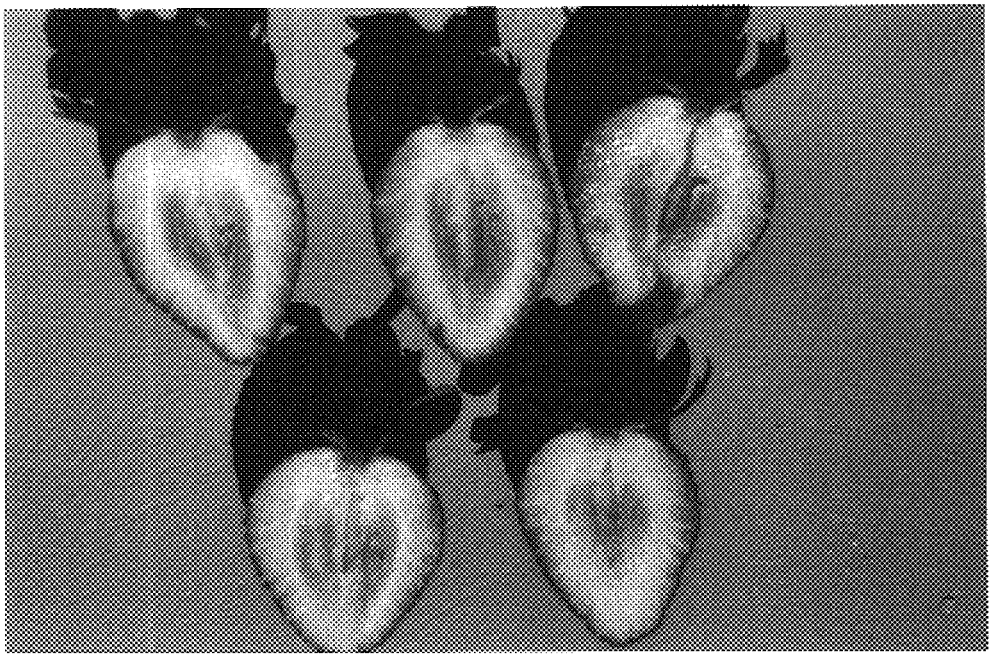
FIG. 5 shows the fruit in longitudinal cross-section.

The following detailed description of the new variety is based upon observations taken of plants and fruit grown in Hillsborough county, Fla., U.S.A. This description is in accordance with UPOV terminology. Observations of 'Driscoll Destin', 'Biscayne' and 'Key Largo' were taken in side by side comparison in the 2003–2004 winter season. Plants for observation were harvested from McArthur, Calif., and held in refrigerated storage until planting in Hillsborough county, Fla. in October 2003. Plants were grown in raised beds of soil under conditions typical of commercial strawberry production in central Florida. Fruits were harvested twice weekly for yield determination from November 2003 to March 2004. Measurements of plant, flower, and fruit characteristics were made in January 2004, approximately four months after planting. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

6.1 PROPAGATION

The new variety is principally propagated by way of stolons. Although propagation by stolons is presently preferred, other known methods of propagating strawberry plants may be employed.

6.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on five month old plants. Fruit and flower measurements are an average of both primary and secondary fruit and flowers.

Table 1 provides information on the plant and fruit characteristics of the new variety 'Driscoll Destin' compared with characteristics of 'Biscayne' and 'Key Largo.' Table 2 provides additional information of the plant and fruit characteristics of the new variety 'Driscoll Destin' compared with characteristics of the varieties 'Biscayne' and 'Key Largo.' Table 3 provides reactions of the new variety to stresses, pests and diseases compared with reactions of the varieties 'Biscayne' and 'Key Largo.' Table 4 provides isozyme characteristics of the new variety as compared to that of the varieties 'Biscayne' and 'Key Largo.'

TABLE 1

QUANTITATIVE COMPARISON OF 'DRISCOLL DESTIN', 'BISCAYNE,' AND 'KEY LARGO'

| | 'Driscoll Destin' | 'Biscayne' | 'Key Largo' |
|---|---|---|---|
| Plant Characteristics | | | |
| Height of Plant (cm) | 8.1 | 10.0 | 11.6 |
| Spread of Plant (cm) | 32.4 | 31.3 | 32.1 |
| Number of Crowns | 3.4 | 3.2 | 4.2 |
| Leaf Characteristics | | | |
| Terminal Leaflet Length (cm) | 8.2 | 7.6 | 8.4 |
| Terminal Leaflet Width (cm) | 8.3 | 8.1 | 8.0 |
| Terminal Leaflet Length/Width Ratio | 0.99 | 0.93 | 1.06 |
| # Teeth/Terminal Leaflet | 24.5 | 27.0 | 21.6 |
| Color of upper side | 135A medium to dark green | 137A light green | 137A light green |
| Color of under side | 136C light gray green | 139C light gray green | 139C light gray green |
| Petiole Length (cm) | 8.6 | 9.2 | 11.5 |
| Petiole Color | 145B yellow green | 142D yellow green | 142D yellow green |
| Petiolule Length (mm) | 7.0 | 5.5 | 6.3 |
| Petiolule Diameter (mm) | 2.1 | 2.2 | 1.9 |

TABLE 1-continued

QUANTITATIVE COMPARISON OF 'DRISCOLL DESTIN', 'BISCAYNE,' AND 'KEY LARGO'

| | 'Driscoll Destin' | 'Biscayne' | 'Key Largo' |
|---|---|---|---|
| Petiolule Color | 145C yellow green | 142D yellow green | 142D yellow green |
| Bract Frequency | 8% typically single | 83% typically paired | 0% |
| Stipule Length (cm) | 3.8 | 3.7 | 3.4 |
| Stipule Width (cm) | 1.6 | 2.0 | 1.5 |
| Stolon Characteristics | | | |
| Anthocyanin color | 60A red | 59B red | |
| Diameter at bract (mm) | 3.59 | 3.24 | 3.30 |
| Avg. # of Daughter plants (2003 Nursery) | 51 | 72 | 52 |
| Flower Characteristics | | | |
| Petal Length (cm) | 1.5 | 1.36 | 1.65 |
| Petal Width (cm) | 1.3 | 1.49 | 1.46 |
| Petal Length/Width Ratio | 1.09 | 0.91 | 1.13 |
| Flower Diameter (cm) | 3.0 | 2.76 | 2.72 |
| Calyx Diameter (cm) | 4.0 | 3.86 | 5.11 |
| Sepal Length (mm) | 15.8 | 15.3 | 21.5 |
| Sepal Width (cm) | 6.6 | 7.22 | 9.15 |
| Petal Color | 155C white | 155C white | 155C white |
| Receptical Color | 150A yellow green | 150A yellow green | 150A yellow green |
| Anther Color | 13A yellow | 9A yellow | 9A yellow |
| Fruiting Truss Length (cm) | 8.8 | 8.7 | 13.6 |
| Fruit Characteristics | | | |
| Fruit Length (cm) | 5.6 | 4.8 | 4.8 |
| Fruit Width (cm) | 4.3 | 4.0 | 3.5 |
| Fruit Length/Width Ratio | 1.31 | 1.20 | 1.37 |
| Average Berry Weight (g) | 28.9 | 26.5 | 23.2 |
| External Color | 45B orange red | 46B red | 46B red |
| Internal Color | 179C orange red | 44A medium red | 44B medium red |
| Achene Coloration | 184B to 150A greyed red to yellow green | 180B to 150C greyed red to yellow green | 182B to 150A greyed red to yellow green |
| Achenes per berry | 194 | 109 | 104 |
| Achene weight (g) | 0.000077 | 0.00046 | 0.00058 |
| 2003–2004 Fruit Yield (g/plant) | 285 | 243 | 251 |

TABLE 2

QUALITATIVE COMPARISON OF 'DRISCOLL DESTIN', 'BISCAYNE,' AND 'KEY LARGO'

| | 'Driscoll Destin' | 'Biscayne' | 'Key Largo' |
|---|---|---|---|
| Plant | | | |
| Habit | flat | flat globose | globose |
| Canopy Density | dense | medium | medium |
| Vigor | strong | strong | medium |
| Leaf | | | |
| Shape in cross section | concave | concave | slightly concave |
| Interveinal blistering | very strong | weak | weak |
| Glossiness | weak | medium | medium |
| Number of leaflets | three only | three only | three only |

TABLE 2-continued

QUALITATIVE COMPARISON OF 'DRISCOLL DESTIN', 'BISCAYNE,' AND 'KEY LARGO'

| | 'Driscoll Destin' | 'Biscayne' | 'Key Largo' |
|---|---|---|---|
| Terminal leaflet margin profile | revolute to flat | revolute | revolute |
| Terminal leaflet shape of base | obtuse | rounded | slightly oblique |
| Terminal leaflet shape of teeth | acute to obtuse | rounded | rounded |
| Stipule pubescence | very dense | medium | medium |
| Petiole pubescence | medium | medium | medium |
| Petiole pose of hairs | outwards | outwards | upwards |
| Stolon | | | |
| Anthocyanin coloration | medium | strong | |
| Thickness | thick | medium | |
| Pubescence | medium | medium | |
| Inflorescence | | | |
| Position relative to foliage | beneath | level | level to above |
| Diameter of calyx relative to corolla on secondary flowers | same size | larger | much larger |
| Diameter of inner calyx relative to outer on secondary flowers | same size to larger | same size | smaller |
| Spacing of petals | overlapping | overlapping | overlapping |
| Fruiting Truss | | | |
| Attitude at first picking | prostrate | prostrate | semi-erect |
| Fruit | | | |
| Predominant shape | conical to almost cylindrical | conical | conical |
| Difference in shapes between primary and secondary fruits | moderate | slight | slight |
| Band without achenes | medium | narrow | narrow |

TABLE 2-continued

QUALITATIVE COMPARISON OF 'DRISCOLL DESTIN', 'BISCAYNE,' AND 'KEY LARGO'

| | 'Driscoll Destin' | 'Biscayne' | 'Key Largo' |
|---|---|---|---|
| Unevenness of surface | weak | weak | weak |
| Evenness of color | uneven | even | even |

6.4 ISOZYME ANALYSIS

In addition to the morphological description above, the new cultivar 'Driscoll Destin' has been analyzed to obtain an indication of its genetic makeup to provide further means for identifying the new variety and distinguishing it from other somewhat similar and/or related strawberry varieties. Specifically, leaf samples of 'Driscoll Destin', 'Biscayne' and 'Key Largo' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL DESTIN', 'BISCAYNE,' AND 'KEY LARGO'

| Locus | 'Driscoll Destin' | 'Biscayne' | 'Key Largo' |
|---|---|---|---|
| PGI | A2 | A1 | A1 |
| LAP | B3 | B3 | B3 |
| PGM | C2 | C4 | C4 |

What is claimed:

1. A new and distinct variety of strawberry plant, substantially as shown and described.

* * * * *